US00PP22189P2

(12) United States Plant Patent
Adam, Jr.

(10) Patent No.: US PP22,189 P2
(45) Date of Patent: Oct. 4, 2011

(54) ***TIARRELLA* PLANT NAMED 'FM MOOBERRY'**

(50) Latin Name: *Tiarella cordifolia*
Varietal Denomination: FM Mooberry

(75) Inventor: Sinclair A. Adam, Jr., Coatesville, PA (US)

(73) Assignee: Plants Nouveau—a division of Treadwell Palmer International Inc., Baltimore, MD (US)

( * ) Notice: Subject to any disclaimer, the term of this patent is extended or adjusted under 35 U.S.C. 154(b) by 0 days.

(21) Appl. No.: 12/806,640

(22) Filed: Aug. 18, 2010

(51) Int. Cl.
*A01H 5/00* (2006.01)

(52) U.S. Cl. ..... Plt./486

(58) Field of Classification Search ..... Plt./486
See application file for complete search history.

*Primary Examiner* — Annette Para
(74) *Attorney, Agent, or Firm* — Penny J. Aguirre

(57) ABSTRACT

A new cultivar of *Tiarella cordifolia*, 'FM Mooberry', characterized by its compact mounding clump growth habit, its white flowers on single and branched flower racemes, its unique foliage coloration with ovate-shaped green leaves with maroon markings in the center that expand to a greater area and become darker in color as the leaves mature in late summer, and its ability to form dense stands particularly suited for garden border planting, ornamental ground cover, shaded areas, and ecology and restoration planting.

2 Drawing Sheets

Botanical classification: *Tiarella cordifolia.*
Cultivar designation: 'FM Mooberry'.

CROSS REFERENCE TO A RELATED APPLICATION

This application is co-pending with a U.S. Plant Patent Application filed for a plant derived the Inventor's breeding program that is entitled *Tiarella* Plant Named 'Stephanie Cohen' (U.S. Plant patent application Ser. No. 12/806,647).

BACKGROUND OF THE INVENTION

The present invention relates to a new and distinct cultivar of *Tiarella* plant, botanically known as *Tiarella cordifolia* 'FM Mooberry' and will be referred to hereafter by its cultivar name, 'FM Mooberry'.

The Inventor discovered the new cultivar, 'FM Mooberry', in a trial plot at his nursery in Coatesville, Pa., in 2007. The parentage of the new variety is the result of open-pollinated plants of *Tiarella cordifolia*, and *Tiarella cordifolia* var. *collina*. The exact parentage is unknown as several hundred cultivars and unnamed plants from the Inventors breeding program were grown for seed production. The new cultivar, 'FM Mooberry', was selected for its unique growth habit, flower stem branching, and distinctive foliage coloration throughout the growing season.

Asexual reproduction of the new cultivar was first accomplished by division in Coatesville, Pa. by the Inventor in 2007. Propagation by division and subsequently by tissue culture has determined that the characteristics of this cultivar are stable and are reproduced true to type in successive generations.

SUMMARY OF THE INVENTION

The following traits have been repeatedly observed and represent the characteristics of 'FM Mooberry'. These attributes in combination distinguish 'FM Mooberry' as a new and distinct cultivar of *Tiarella.*

1. 'FM Mooberry' exhibits a compact mounding clump growth habit.
2. 'FM Mooberry' exhibits white flowers on single and branched flower racemes.
3. 'FM Mooberry' exhibits unique foliage coloration with ovate-shaped green leaves with dark maroon markings in the center. The markings expand to a greater area and become darker in color as the leaves mature in late summer.
4. 'FM Mooberry' forms form dense stands particularly suited for garden border planting, ornamental ground cover, shaded areas, and ecology and restoration planting.

'FM Mooberry' can be most closely compared to 'Stephanie Cohen', which is similar in having a clump-forming plant habit. 'Stephanie Cohen' differs most significantly from 'FM Mooberry' in having leaves that are deeply lobed with smaller maroon marking and in being very glossy when in full bloom. In addition, the white flowers of 'Stephanie Cohen' emerge from pink flower buds. 'FM Mooberry' can also be compared the cultivar 'Brandywine' (not patented), which is similar in having a clump-forming plant habit. 'Brandywine' differs from 'FM Mooberry' in being a larger plant and in having solid green foliage that lacks markings.

BRIEF DESCRIPTION OF THE DRAWING

The accompanying colored photographs illustrate the overall appearance and distinct characteristics of the new *Tiarella*. The photographs were taken of two year-old plants of 'FM Mooberry' as grown outdoors in one-gallon containers in Coatesville, Pa.

The photograph in FIG. 1 was taken in April and illustrates the spring foliage and flower buds.

Figure 1:
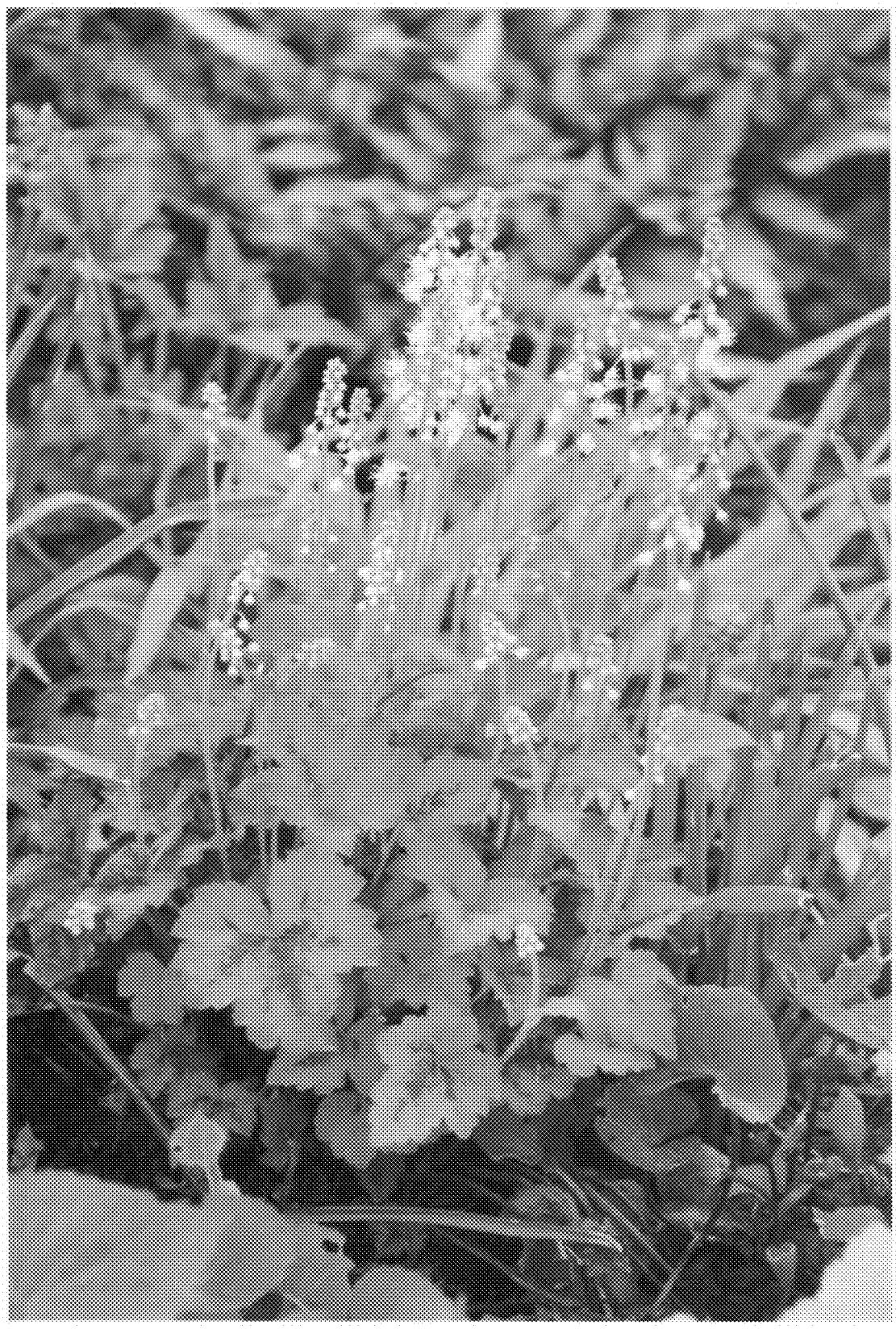
Figure 2:
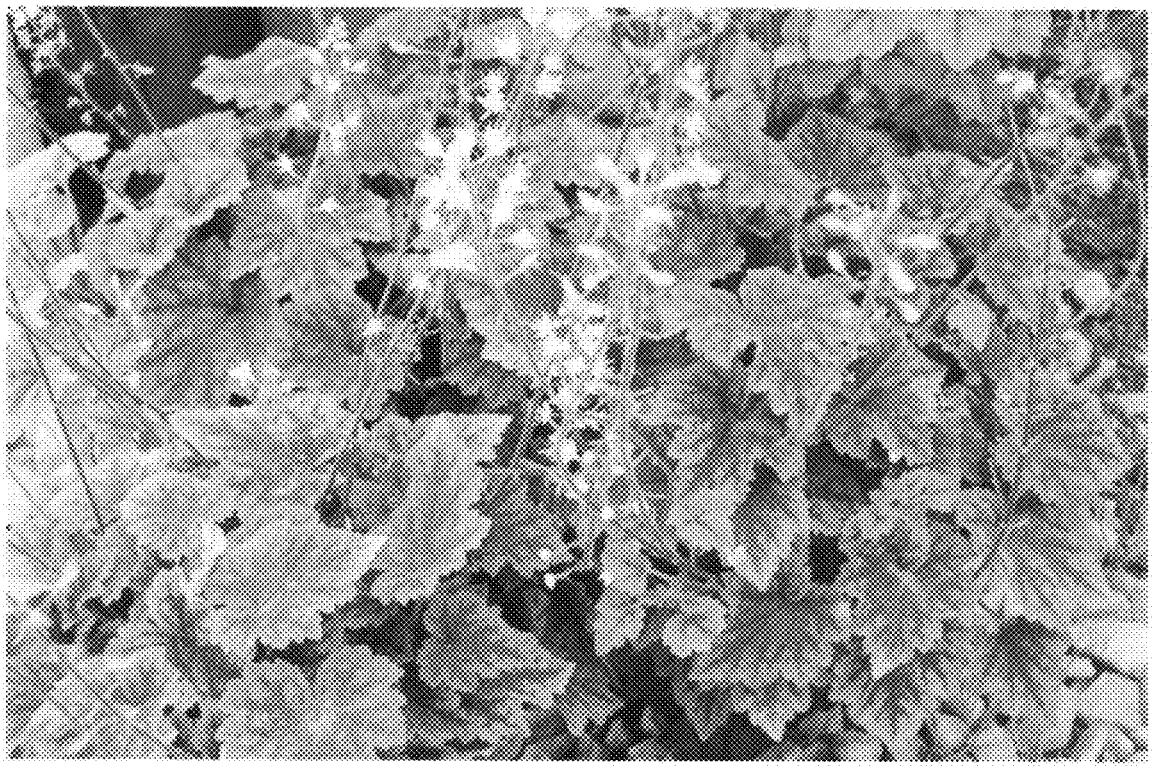

The photograph in FIG. 2 was taken in May and provides a close-up view of the mature foliage and blooms of 'FM Mooberry'. The colors in the photographs are as close as possible with the digital photography and printing techniques utilized and the color codes in the detailed botanical description more accurately describe the colors of the new *Tiarella*.

DETAILED BOTANICAL DESCRIPTION OF THE PLANT

The following is a detailed description of two-year-old plants grown outdoors and in the greenhouse in one-gallon containers during 2007 and 2008 at Coatesville, Pa., USA. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Botanical classification: 'FM Mooberry' is a cultivar of *Tiarella cordifolia*.

General characteristics:

*Plant type.*—Perennial, evergreen.

*Plant habit.*—Compact mounding clump-forming.

*Blooming.*—Abundant in May and June, and sporadically thereafter during the summer and fall.

*Plant height.*—Approximately 10 to 12 cm without blooms, and approximately 28 to 32 cm with blooms.

*Plant width.*—Approximately 18 to 20 cm (1 year plant), 28 to 30 cm (2 year plant).

*Diseases and pests.*—No susceptibility to diseases has been noted during observations to date.

*Root description.*—Fibrous roots, branched racemes occasionally root.

*Hardiness.*—U.S.D.A. Zones 4 to 7.

*Branching habit.*—Basal rosette.

*Propagation.*—Division and tissue culture.

*Vigor.*—Moderate.

Foliage description:

*Leaf shape.*—Cordate to ovate, slightly lobed, with 5 lobes the central one being more pronounced, lobes broadly obtuse to rounded and cuspidate.

*Leaf division.*—Simple.

*Leaf margins.*—Crenate at leaf maturity, doubly serrate in juvenility.

*Leaf size.*—Approximately 7 to 8 cm in length and 6 to 7 cm in width.

*Leaf apex.*—Acute to rounded.

*Leaf base.*—Cordate.

*Leaf surface.*—Slightly rugose, upper surface; slightly glossy, setulose with setae 2 to 3 mm in length and NN155C in color, lower surface; glabrous, velvet matte, texture contrast more evident in fall foliage coloration.

*Leaf arrangement.*—Basal clump.

*Leaf venation.*—Palmately reticulate, upper surface; fine, slightly translucent, 144C in color, lower surface; raised, pubescent, color a blend of 148C and 144C.

*Leaf color.*—Summer emerging upper surface; N144A with 187C at center and along main vein, summer emerging lower surface; 146B to 146C, summer mature upper surface; 143B to 146C with 187A in center and along main vein, summer mature lower surface; N144D, fall mature upper and lower surface; exhibits light and darker patches varying in colors from 49D, N77A, 53D, 186B, 187A to 187B.

*Leaf attachment.*—Petiolate.

*Petiole.*—Approximately 6 to 10 cm in length and 1 to 2 mm in diameter, 197B suffused with 182C, surface pubescent with hairs 1 to 2 mm in length, NN155C in color.

Inflorescence description:

*Inflorescence Type.*—Raceme and perfect (bisexual).

*Bearing.*—On a branched stalk commonly having a height of approximately 28 to 32 cm, with a cauline leaf, subsequently, branched racemes emerge, bearing a cauline leaf at the side branch.

*Inflorescence size.*—About 15 cm in length (from base of raceme) and 4 cm in width.

*Number of blooms per raceme.*—Approximately 35 to 50 blooms.

*Flower size.*—Approximately 5 to 7 mm in length and 3 mm in width.

*Flower buds.*—Globose in shape, about 3 mm in length and 2 mm in width, NN155B in color.

*Flower fragrance.*—Slight and sweet.

*Lastingness of flowers.*—About 4 days.

*Calyx.*—Five-lobed, sepals fused at base, 145D in color.

*Petals.*—Five, triangular in shape, surface glabrous, color upper surface NN155C, color lower surface NN155B.

*Pedicel.*—Approximately 6 to 7 mm in length and 1.5 mm in width, surface pubescent, color N77D.

*Androecium.*—10 stamens, anthers 168A in color, pollen not observed.

*Gynoecium.*—1 pistil.

*Fruit/seeds.*—Approximately 600 seeds, 0.2 grams per plant.

It is claimed:

1. A new and distinct cultivar of *Tiarella* plant named 'FM Mooberry' as herein illustrated and described.

* * * * *

UNITED STATES PATENT AND TRADEMARK OFFICE

CERTIFICATE OF CORRECTION

PATENT NO. : PP22,189 P2
APPLICATION NO. : 12/806640
DATED : October 4, 2011
INVENTOR(S) : Sinclair A. Adam, Jr.

It is certified that error appears in the above-identified patent and that said Letters Patent is hereby corrected as shown below:

Title Page, Item (54) in the title, "TIARRELLA" should correctly read --TIARELLA--.

Signed and Sealed this
Twenty-fifth Day of October, 2011

David J. Kappos

David J. Kappos
*Director of the United States Patent and Trademark Office*